US010777849B2

United States Patent
Lee et al.

(10) Patent No.: US 10,777,849 B2
(45) Date of Patent: Sep. 15, 2020

(54) NON-AQUEOUS ELECTROLYTE SOLUTION AND LITHIUM SECONDARY BATTERY INCLUDING THE SAME

(71) Applicant: LG Chem, Ltd., Seoul (KR)

(72) Inventors: Jung Hoon Lee, Daejeon (KR); Kyoung Ho Ahn, Daejeon (KR); Chul Haeng Lee, Daejeon (KR); Jeong Woo Oh, Daejeon (KR)

(73) Assignee: LG Chem, Ltd. (KR)

( * ) Notice: Subject to any disclaimer, the term of this patent is extended or adjusted under 35 U.S.C. 154(b) by 131 days.

(21) Appl. No.: 16/307,751

(22) PCT Filed: Jan. 12, 2018

(86) PCT No.: PCT/KR2018/000646
§ 371 (c)(1),
(2) Date: Dec. 6, 2018

(87) PCT Pub. No.: WO2018/131952
PCT Pub. Date: Jul. 19, 2018

(65) Prior Publication Data
US 2019/0198925 A1    Jun. 27, 2019

(30) Foreign Application Priority Data

Jan. 12, 2017 (KR) ............. 10-2017-0005598
Jan. 12, 2018 (KR) ............. 10-2018-0004664

(51) Int. Cl.
*H01M 10/0567* (2010.01)
*H01M 10/0525* (2010.01)
(Continued)

(52) U.S. Cl.
CPC ...... *H01M 10/0567* (2013.01); *C07D 251/30* (2013.01); *C08G 18/3812* (2013.01);
(Continued)

(58) Field of Classification Search
CPC ......... H01M 10/0567; H01M 10/0525; H01M 10/0234; C08G 65/48; C08K 3/32
See application file for complete search history.

(56) References Cited

U.S. PATENT DOCUMENTS 8,524,399 B2  9/2013 Kim et al.
2011/0020700 A1 1/2011 Iwaya
(Continued)

FOREIGN PATENT DOCUMENTS

JP  2012160316 A  8/2012
KR  2005-0083532 A  8/2005
(Continued)

OTHER PUBLICATIONS

Extended European Search Report including Written Opinion for Application No. EP18739272.5 dated Apr. 29, 2019.
(Continued)

*Primary Examiner* — Kenneth J Douyette
(74) *Attorney, Agent, or Firm* — Lerner, David, Littenberg, Krumholz & Mentlik, LLP

(57) ABSTRACT

The present invention relates to a non-aqueous electrolyte solution including a non-aqueous organic solvent, a lithium salt, and an oligomer represented by Formula 1 described in the present specification, and a lithium secondary battery including the same. Since the non-aqueous electrolyte solution according to an embodiment of the present invention may reduce gas, such as CO or $CO_2$, generated in the secondary battery during high-temperature storage, it may further improve high-temperature stability of the lithium secondary battery.

14 Claims, 1 Drawing Sheet

(51) Int. Cl.
*C08G 65/48* (2006.01)
*C08K 3/32* (2006.01)
*C08G 18/50* (2006.01)
*C08G 18/38* (2006.01)
*C08G 65/00* (2006.01)
*C08G 65/333* (2006.01)
*H01M 10/052* (2010.01)
*C08G 18/67* (2006.01)
*C07D 251/30* (2006.01)
*C08J 3/09* (2006.01)
*H01M 10/0569* (2010.01)

(52) U.S. Cl.
CPC ....... *C08G 18/5015* (2013.01); *C08G 18/672* (2013.01); *C08G 65/007* (2013.01); *C08G 65/33317* (2013.01); *C08G 65/48* (2013.01); *C08J 3/095* (2013.01); *C08K 3/32* (2013.01); *H01M 10/052* (2013.01); *H01M 10/0525* (2013.01); *C08K 2201/001* (2013.01); *H01M 10/0569* (2013.01); *H01M 2300/0025* (2013.01); *H01M 2300/0037* (2013.01)

(56) References Cited

U.S. PATENT DOCUMENTS

| 2011/0183216 A1 | 7/2011 | Kim et al. |
| 2014/0272606 A1* | 9/2014 | Chu ................ H01M 10/0568 429/332 |
| 2015/0364794 A1 | 12/2015 | Nakazawa et al. |
| 2017/0229735 A1 | 8/2017 | Ahn et al. |

FOREIGN PATENT DOCUMENTS

| KR | 2009-0015859 A | 2/2009 |
| KR | 2011-0008172 A | 1/2011 |
| KR | 2011-0010516 A | 2/2011 |
| KR | 2015-0125928 A | 11/2015 |
| KR | 2016-0040127 A | 4/2016 |
| WO | 2016161465 A1 | 10/2016 |

OTHER PUBLICATIONS

Search report from International Application No. PCT/KR2018/000646, dated Apr. 20, 2018.

Wong, H. C., Thesis: "Perfluoropolyether-Based Electrolytes for Lithium Battery Applications", 2015, Department of Chemistry, University of North Carolina at Chapel Hill, pp. 100-111, and Figure 4.9.

Gong, X. et al., "Facile One Pot Polycondensation Method to Synthesize the Crosslinked Polyethylene Glycol-Based Copolymer Electrolytes", Macromolecular Chemistry and Physics, 2016, vol. 217, pp. 1607-1613.

* cited by examiner

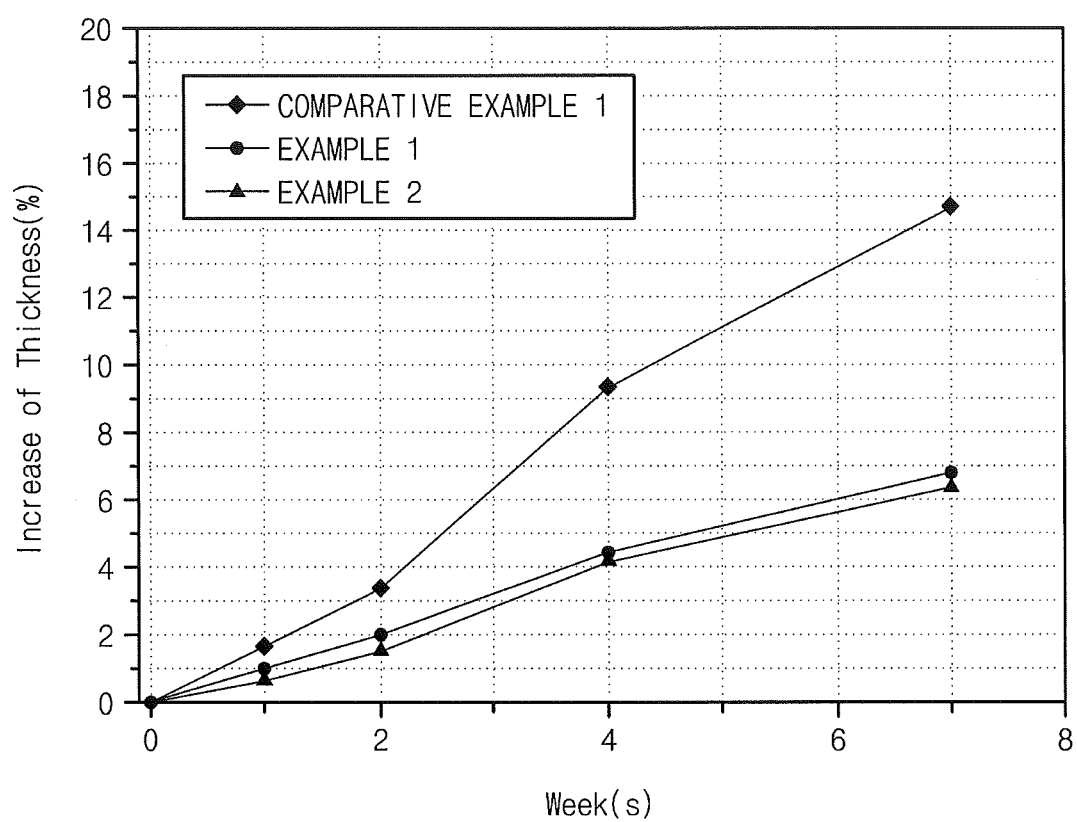

NON-AQUEOUS ELECTROLYTE SOLUTION AND LITHIUM SECONDARY BATTERY INCLUDING THE SAME

CROSS-REFERENCE TO RELATED APPLICATIONS

This application is a national phase entry under 35 U.S.C. § 371 of International Application No. PCT/KR2018/000646, filed Jan. 12, 2018, which claims priority to Korean Patent Application No. 10-2017-0005598, filed Jan. 12, 2017, and Korean Patent Application No. 10-2018-0004664, filed Jan. 12, 2018, the disclosures of which are incorporated herein by reference.

TECHNICAL FIELD

The present invention relates to a non-aqueous electrolyte solution including an oligomer additive, and a lithium secondary battery including the same.

BACKGROUND ART

Recently, interests in energy storage technologies have been increasingly grown. In particular, while the application of the energy storage technologies is expanded to mobile phones, camcorders, notebook PCs, and even to electric vehicles, research and efforts for the development of the energy storage technologies have been gradually materialized.

Electrochemical devices have received most attention in the field of energy storage technologies, and there emerges an interest in rechargeable secondary batteries among these electrochemical devices.

Among the currently used secondary batteries, lithium secondary batteries, developed in the early 1990's, are spotlighted because the lithium secondary batteries may have higher operating voltage and significantly higher energy density.

The lithium secondary battery includes a positive electrode, a negative electrode, a separator disposed between the positive electrode and the negative electrode, and a non-aqueous electrolyte solution including an electrolyte solution solvent and an electrolyte salt.

Since the electrolyte solution solvent is decomposed on a surface of an electrode during charge and discharge of the battery or collapses a negative electrode structure by being co-intercalated between the carbon negative electrode layers, the electrolyte solution solvent may degrade stability of the battery.

It is known that this limitation may be addressed by a solid electrolyte interface (SEI) film which is formed on the surface of the negative electrode by the reduction of the electrolyte solution solvent during initial charge of the battery.

However, the SEI film may be easily collapsed over time by electrochemical energy and thermal energy when the lithium secondary battery is operated or left standing in a high-temperature environment. In a case in which the SEI film is collapsed, the negative electrode is exposed, and gases, such as $CO$, $CO_2$, $CH_4$, and $C_2H_6$, are generated while the exposed negative electrode reacts with the electrolyte solution to continuously cause a side reaction.

As a result, since a battery internal pressure increases to cause an internal short circuit of the battery as well as battery deformation such as battery swelling, fire or explosion of the battery may occur.

Recently, a method of adding an additive for forming an SEI film to prevent the collapse of the SEI film in the non-aqueous electrolyte solution has been proposed. However, eventually another limitation has occurred in which irreversible capacity of the secondary battery is increased and output characteristic are reduced while an electrolyte solution oxidation reaction occurs on the surface of a positive electrode during a high-temperature reaction due to the electrolyte solution additive.

In order to address these limitations, there is a need to develop a non-aqueous electrolyte solution and a lithium secondary battery which may reduce gas generation during high-temperature storage.

PRIOR ART DOCUMENT

Korean Patent Application Laid-open Publication No. 2009-0015859

DISCLOSURE OF THE INVENTION

Technical Problem

The present invention is provided to solve these problems.

An aspect of the present invention provides a non-aqueous electrolyte solution which may reduce gas generation during high-temperature storage.

Another aspect of the present invention provides a lithium secondary battery in which high-temperature storage stability is improved by including the non-aqueous electrolyte solution.

Technical Solution

According to an aspect of the present invention, there is provided a non-aqueous electrolyte solution including:
a lithium salt; a non-aqueous organic solvent; and
an oligomer represented by Formula 1 as an additive:

[Formula 1]

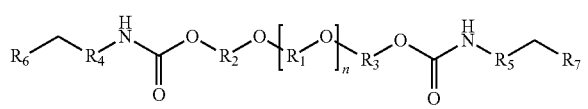

wherein, in Formula 1,
$R_1$ to $R_3$ are each independently a fluorine-substituted or unsubstituted alkylene group having 1 to 4 carbon atoms,
$R_4$ and $R_5$ are each independently an aliphatic hydrocarbon group or an aromatic hydrocarbon group,
$R_6$ and $R_7$ are each independently an alkyl group having 1 to 10 carbon atoms or

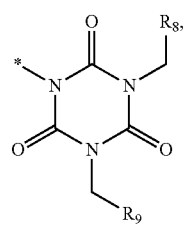

$R_8$ and $R_9$ are each independently an alkyl group having 1 to 10 carbon atoms or

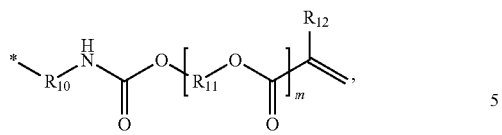

in this case, $R_{10}$ is an aliphatic hydrocarbon group or an aromatic hydrocarbon group, $R_{11}$ is an alkylene group having 1 to 3 carbon atoms, $R_{12}$ is hydrogen or an alkyl group having 1 to 2 carbon atoms, n is an integer of 1 to 70, and m is an integer of 1 to 3.

In the oligomer represented by Formula 1, the aliphatic hydrocarbon groups $R_4$, $R_5$ and $R_{10}$ may include an alicyclic hydrocarbon group or a linear hydrocarbon group.

The alicyclic hydrocarbon group may include at least one selected from the group consisting of a substituted or unsubstituted cycloalkylene group having 4 to 20 carbon atoms; a substituted or unsubstituted cycloalkylene group having 4 to 20 carbon atoms which contains an isocyanate group (NCO); a substituted or unsubstituted cycloalkenylene group having 4 to 20 carbon atoms; and a substituted or unsubstituted heterocycloalkylene group having 2 to 20 carbon atoms.

The linear hydrocarbon group may include at least one selected from the group consisting of a substituted or unsubstituted alkylene group having 1 to 20 carbon atoms; a substituted or unsubstituted alkylene group having 1 to 20 carbon atoms which contains an isocyanate group (NCO); a substituted or unsubstituted alkoxylene group having 1 to 20 carbon atoms; a substituted or unsubstituted alkenylene group having 2 to 20 carbon atoms; and a substituted or unsubstituted alkynylene group having 2 to 20 carbon atoms.

Also, in the oligomer represented by Formula 1, the aromatic hydrocarbon groups of $R_4$, $R_5$ and $R_{10}$ may include a substituted or unsubstituted arylene group having 6 to 20 carbon atoms; or a substituted or unsubstituted heteroarylene group having 2 to 20 carbon atoms.

Specifically, the oligomer represented by Formula 1 may include an oligomer represented by Formula 1a below.

[Formula 1a]

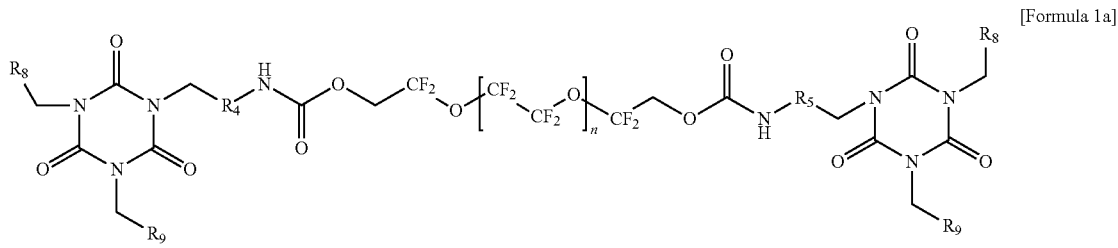

In Formula 1a, $R_4$ and $R_5$ are each independently an aliphatic hydrocarbon group, $R_8$ and $R_9$ are each independently

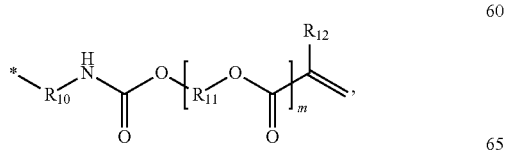

$R_{10}$ is an aliphatic hydrocarbon group, $R_{11}$ is an alkylene group having 1 to 3 carbon atoms, $R_{12}$ is hydrogen or an alkyl group having 1 to 2 carbon atoms, n is an integer of 10 to 20, and m is an integer of 1 to 2.

Specifically, the oligomer represented by Formula 1a may include an oligomer represented by Formula 1a-1 below.

[Formula 1a-1]

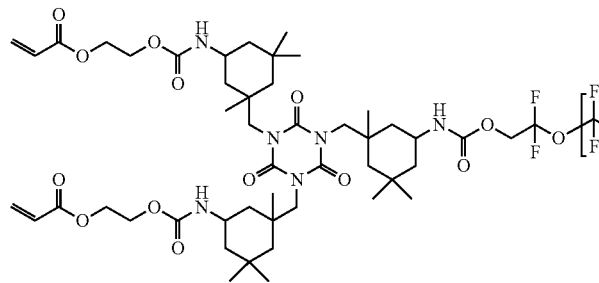 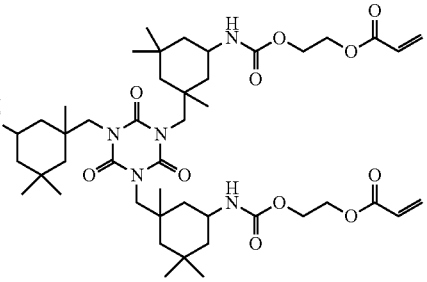

In Formula 1a-1, n is an integer of 10 to 20.

In the non-aqueous electrolyte solution of the present invention, the oligomer represented by Formula 1 may be included in an amount of 0.5 wt % to 20 wt %, for example, 1 wt % to 10 wt % based on a total weight of the non-aqueous electrolyte solution.

Also, the oligomer represented by Formula 1 may have a weight-average molecular weight (Mw) of 1,000 g/mol to 10,000 g/mol, particularly 3,000 g/mol to 8,000 g/mol, and more particularly 3,000 g/mol to 5,000 g/mol.

According to another aspect of the present invention, there is provided a lithium secondary battery including a negative electrode, a positive electrode, a separator disposed between the negative electrode and the positive electrode, and the non-aqueous electrolyte solution of the present invention.

Advantageous Effects

According to an embodiment of the present invention, a non-aqueous electrolyte solution for a lithium secondary battery, which may reduce gas, such as CO or $CO_2$, generated in the secondary battery during high-temperature storage, may be prepared by including an oligomer having a specific structure as an additive. Also, a lithium secondary battery, in which high-temperature storage stability is improved by including the same, may be prepared.

BRIEF DESCRIPTION OF THE DRAWINGS

The following drawings attached to the specification illustrate preferred examples of the present invention by example, and serve to enable technical concepts of the present invention to be further understood together with detailed description of the invention given below, and therefore the present invention should not be interpreted only with matters in such drawings.

The FIGURE is a graph showing the results of measurement of thickness increase rates (%) during high-temperature storage of lithium secondary batteries in Experimental Example 1 of the present invention.

MODE FOR CARRYING OUT THE INVENTION

Hereinafter, the present invention will be described in more detail.

It will be understood that words or terms used in the specification and claims shall not be interpreted as the meaning defined in commonly used dictionaries. It will be further understood that the words or terms should be interpreted as having a meaning that is consistent with their meaning in the context of the relevant art and the technical idea of the invention, based on the principle that an inventor may properly define the meaning of the words or terms to best explain the invention.

Unless otherwise specified in the present invention, the expression "*" denotes the same or different atom or a portion connected between ends of a formula.

In an embodiment of the present invention, provided is a non-aqueous electrolyte solution which includes:

a lithium salt;

a non-aqueous organic solvent; and an oligomer represented by the following Formula 1 as an additive.

[Formula 1]

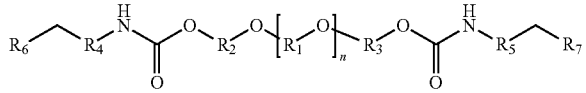

In Formula 1, $R_1$ to $R_3$ are each independently a fluorine-substituted or unsubstituted alkylene group having 1 to 4 carbon atoms, $R_4$ and $R_5$ are each independently an aliphatic hydrocarbon group or an aromatic hydrocarbon group, $R_6$ and $R_7$ are each independently an alkyl group having 1 to 10 carbon atoms or

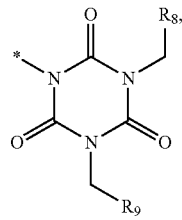

$R_8$ and $R_9$ are each, independently, an alkyl group having 1 to 10 carbon atoms or

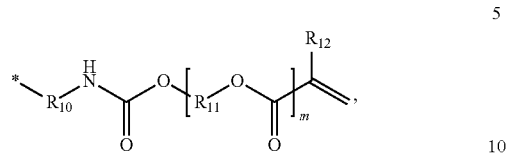

$R_{10}$ is an aliphatic hydrocarbon group or an aromatic hydrocarbon group, $R_{11}$ is an alkylene group having 1 to 3 carbon atoms, $R_{12}$ is hydrogen or an alkyl group having 1 to 2 carbon atoms, n is an integer of 1 to 70, and m is an integer of 1 to 3.

In this case, in the oligomer represented by Formula 1, the aliphatic hydrocarbon groups of $R_4$, $R_5$ and $R_{10}$ may include an alicyclic hydrocarbon group or a linear hydrocarbon group.

The alicyclic hydrocarbon group may include at least one selected from the group consisting of a substituted or unsubstituted cycloalkylene group having 4 to 20 carbon atoms; a substituted or unsubstituted cycloalkylene group having 4 to 20 carbon atoms which contains an isocyanate group (NCO); a substituted or unsubstituted cycloalkenylene group having 4 to 20 carbon atoms; and a substituted or unsubstituted heterocycloalkylene group having 2 to 20 carbon atoms.

The linear hydrocarbon group may include at least one selected from the group consisting of a substituted or unsubstituted alkylene group having 1 to 20 carbon atoms; a substituted or unsubstituted alkylene group having 1 to 20 carbon atoms which contains an isocyanate group (NCO); a substituted or unsubstituted alkoxylene group having 1 to 20 carbon atoms; a substituted or unsubstituted alkenylene group having 2 to 20 carbon atoms; and a substituted or unsubstituted alkynylene group having 2 to 20 carbon atoms.

Also, in the oligomer represented by Formula 1, the aromatic hydrocarbon groups of $R_4$, $R_5$ and $R_{10}$ may include a substituted or unsubstituted arylene group having 6 to 20 carbon atoms; or a substituted or unsubstituted heteroarylene group having 2 to 20 carbon atoms.

Specifically, the oligomer represented by Formula 1 may include an oligomer represented by Formula 1a below.

[Formula 1a]

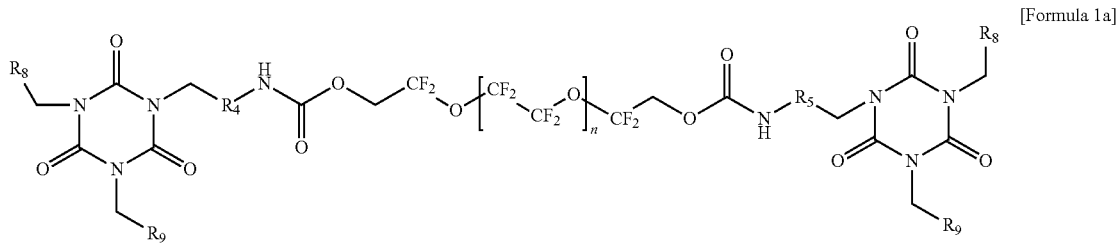

In Formula 1a, $R_4$ and $R_5$ are each independently an aliphatic hydrocarbon group, $R_8$ and $R_9$ are each independently

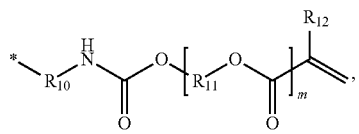

$R_{10}$ is an aliphatic hydrocarbon group, $R_{11}$ is an alkylene group having 1 to 3 carbon atoms, $R_{12}$ is hydrogen or an alkyl group having 1 to 2 carbon atoms, n is an integer of 10 to 20, and m is an integer of 1 to 2.

Specifically, the oligomer represented by Formula 1a may include an oligomer represented by Formula 1a-1 below.

[Formula 1a-1]

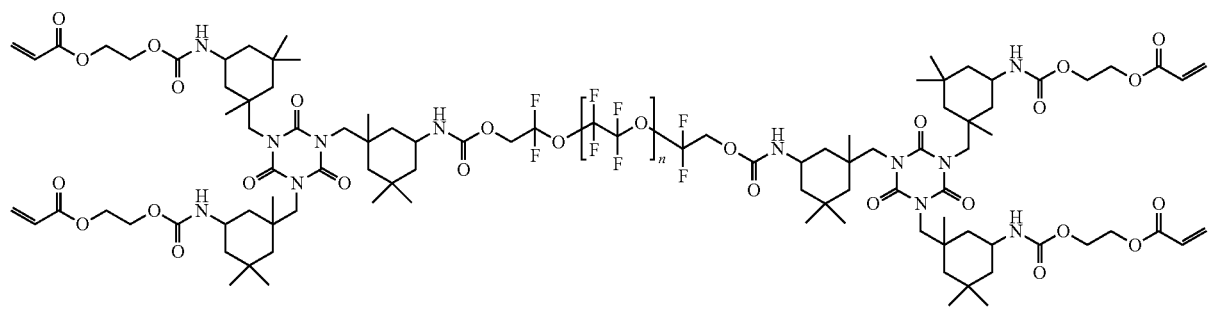

In Formula 1a-1, n is an integer of 10 to 20.

Since the oligomer represented by Formula 1, which is used as an additive of the non-aqueous electrolyte solution of the present invention, contains a fluorine-substituted ethylene group as a hydrophobic portion as well as an acrylate-based functional group as a hydrophilic portion capable of forming a crosslink at both ends by itself, it acts as a surfactant in the battery to be able to reduce surface resistance of an electrode interface. Therefore, the non-aqueous electrolyte solution including the oligomer represented by Formula 1 may have a more improved wetting effect. In addition, since the oligomer represented by Formula 1 has ability to dissociate the lithium salt, it may improve lithium ion mobility. In particular, since the oligomer represented by Formula 1 contains a fluorine-substituted ethylene group having high electrochemical stability and low reactivity with lithium (Li) ions as a repeating unit of a main chain, it may control a side reaction of the lithium ions ($Li^+$) and a decomposition reaction of the lithium salt, and thus, the generation of gas, such as CO or $CO_2$, during overcharge or high-temperature storage may be reduced. Therefore, since the oligomer represented by Formula 1 may prevent the occurrence of battery deformation or an internal short circuit of the battery, the oligomer represented by Formula 1 may improve high-temperature storage stability of the lithium secondary battery.

According to an embodiment of the present invention, the oligomer represented by Formula 1, as the non-aqueous electrolyte solution additive, may be included in an amount of 0.5 wt % to 20 wt %, for example, 1 wt % to 10 wt % based on a total weight of the non-aqueous electrolyte solution.

In a case in which the amount of the additive is less than 0.5 wt %, an effect of reducing gas generation may be insignificant, and, in a case in which the amount of the additive is greater than 20 wt %, since resistance is increased due to the excessive amount of the oligomer, cycle characteristics may be reduced.

Also, according to an embodiment of the present invention, a weight-average molecular weight (Mw) of the oligomer represented by Formula 1 may be controlled by the number of repeating units, and may be in a range of about 1,000 g/mol to about 10,000 g/mol, particularly 3,000 g/mol to 8,000 g/mol, and more particularly 3,000 g/mol to 5,000 g/mol.

In a case in which the weight-average molecular weight of the oligomer is within the above range, a protective layer may be effectively formed on surfaces of a positive electrode and a negative electrode. If the weight-average molecular weight of the oligomer is less than 1,000 g/mol, since the number of the fluorine-substituted repeating units capable of controlling a side reaction of the electrolyte solution is reduced, an effect of suppressing the side reaction between the electrode and the electrolyte solution may be reduced. Also, if the weight-average molecular weight of the oligomer is greater than 10,000 g/mol, since physical properties of the oligomer itself become rigid and an affinity to an electrolyte solvent is reduced, dissolution is not only difficult, but viscosity of the prepared electrolyte solution is also significantly increased due to the high molecular weight. Thus, wetting of the non-aqueous electrolyte solution in an electrode and a separator may be reduced, and, accordingly, overall performance of the lithium secondary battery may be degraded.

The weight-average molecular weight may denote a standard polystyrene-equivalent value measured by gel permeation chromatography (GPC), and, unless otherwise specified, a molecular weight may denote the weight-average molecular weight. For example, in the present invention, the GPC conditions are as follows: the weight-average molecular weight is measured by using 1200 series by Agilent Technologies, a PL mixed B column by Agilent Technologies may be used in this case, and tetrahydrofuran (THF) may be used as a solvent.

Any lithium salt used in an electrolyte salt for a lithium secondary battery may be used as the lithium salt included in the non-aqueous electrolyte solution according to the embodiment of the present invention without limitation, and, for example, the lithium salt may include $Li^+$ as a cation, and may include at least one selected from the group consisting of $F^-$, $Cl^-$, $Br^-$, $I^-$, $NO_3^-$, $N(CN)_2^-$, $BF_4^-$, $ClO_4^-$, $AlO_4^-$, $AlCl_4^-$, $PF_6^-$, $SbF_6^-$, $AsF_6^-$, $BF_2C_2O_4^-$, $BC_4O_8^-$, $(CF_3)_2PF_4^-$, $(CF_3)_3PF_3^-$, $(CF_3)_4PF_2^-$, $(CF_3)_5PF^-$, $(CF_3)_6P^-$, $CF_3SO_3^-$, $C_4F_9SO_3^-$, $CF_3CF_2SO_3^-$, $(CF_3SO_2)_2N^-$, $(F_2SO_2)_2N^-$, $CF_3CF_2(CF_3)_2CO^-$, $(CF_3SO_2)_2CH^-$, $CF_3(CF_2)_7SO_3^-$, $CF_3CO_2^-$, $CH_3CO_2^-$, $SCN^-$, and $(CF_3CF_2SO_2)_2N^-$ as an anion. One or, if necessary, a mixture of two or more thereof may be used as the lithium salt. The lithium salt may be appropriately changed in a normally usable range, but may specifically be included in a concentration of 0.8 M to 2 M, for example, 0.8 M to 1.5 M in the electrolyte solution to obtain an optimum effect of forming an anti-corrosion film on the surface of the electrode.

Also, the non-aqueous organic solvent included in the non-aqueous electrolyte solution according to the embodiment of the present invention is not limited as long as it may minimize decomposition due to an oxidation reaction during charge and discharge of the secondary battery and may exhibit desired characteristics with an additive, and, for example, as the non-aqueous organic solvent, an ether-based solvent, an ester-based solvent, or an amide-based solvent may be used alone or in mixture of two or more thereof.

As the ether-based solvent among the organic solvents, any one selected from the group consisting of dimethyl ether, diethyl ether, dipropyl ether, methylethyl ether, methylpropyl ether, and ethylpropyl ether, or a mixture of two or more thereof may be used, but the present invention is not limited thereto.

Furthermore, the ester-based solvent may include at least one compound selected from the group consisting of a cyclic carbonate compound, a linear carbonate compound, a linear ester compound, and a cyclic ester compound.

Among these compounds, specific examples of the cyclic carbonate compound may be any one selected from the group consisting of ethylene carbonate (EC), propylene carbonate (PC), 1,2-butylene carbonate, 2,3-butylene carbonate, 1,2-pentylene carbonate, 2,3-pentylene carbonate, vinylene carbonate, and fluoroethylene carbonate (FEC), or a mixture of two or more thereof.

Also, specific examples of the linear carbonate compound may be any one selected from the group consisting of dimethyl carbonate (DMC), diethyl carbonate (DEC), dipropyl carbonate, ethylmethyl carbonate (EMC), methylpropyl carbonate, and ethylpropyl carbonate, or a mixture of two or more thereof, but the present invention is not limited thereto.

Specific examples of the linear ester compound may be any one selected from the group consisting of methyl acetate, ethyl acetate, propyl acetate, methyl propionate, ethyl propionate, propyl propionate, and butyl propionate, or a mixture of two or more thereof, but the present invention is not limited thereto.

Specific examples of the cyclic ester compound may be any one selected from the group consisting of γ-butyrolactone, γ-valerolactone, γ-caprolactone, δ-valerolactone, and ε-caprolactone, or a mixture of two or more thereof, but the present invention is not limited thereto.

Among the ester-based solvents, since the cyclic carbonate-based compound is well dissociate the lithium salt in the electrolyte due to high permittivity as a highly viscous organic solvent, the cyclic carbonate-based compound may be preferably used. When the above cyclic carbonate-based compound is mixed with the low viscosity, low permittivity linear carbonate-based compound, such as dimethyl carbonate and diethyl carbonate, and the linear ester-based compound in an appropriate ratio, an electrolyte solution having high electrical conductivity may be more prepared.

The non-aqueous electrolyte solution for a lithium secondary battery according to the embodiment of the present invention may further include an additional additive, if necessary. As the additional additive which may be used in the present invention, vinylene carbonate, vinyl ethylene carbonate, fluoroethylene carbonate, cyclic sulfite, saturated sultone, unsaturated sultone, and a non-cyclic sulfone may be used alone or in a mixture of two or more thereof.

In this case, the cyclic sulfite may include ethylene sulfite, methyl ethylene sulfite, ethyl ethylene sulfite, 4,5-dimethyl ethylene sulfite, 4,5-diethyl ethylene sulfite, propylene sulfite, 4,5-dimethyl propylene sulfite, 4,5-diethyl propylene sulfite, 4,6-dimethyl propylene sulfite, 4,6-diethyl propylene sulfite, and 1,3-butylene glycol sulfite, the saturated sultone may include 1,3-propane sultone and 1,4-butane sultone, the unsaturated sultone may include ethene sultone, 1,3-propene sultone, 1,4-butene sultone, and 1-methyl-1,3-propene sultone, and the non-cyclic sulfone may include divinyl sulfone, dimethyl sulfone, diethyl sulfone, methyl ethyl sulfone, and methyl vinyl sulfone.

The additional additives may be used as a mixture of two or more thereof, and may be included in an amount of 0.01 wt % to 5 wt %, particularly 0.01 wt % to 3 wt %, and more particularly 0.05 wt % to 3 wt % based on the total weight of the electrolyte solution. If the amount of the additional additive is less than 0.01 wt %, effects of improving low-temperature output of the battery and improving high-temperature storage characteristics and high-temperature life characteristics are insignificant, and, if the amount of the additional additive is greater than 5 wt %, there is a possibility that the side reaction in the electrolyte solution excessively occurs during charge and discharge of the battery. In particular, since the additional additives are not sufficiently decomposed at high temperature when the additional additives are excessively added, the additional additives may be present as unreacted materials or precipitates in the electrolyte solution at room temperature. Accordingly, a side reaction may occur in which lifetime or resistance characteristics of the secondary battery are reduced.

Also, in an embodiment of the present invention, provided is a lithium secondary battery including a positive electrode, a negative electrode, a separator disposed between the positive electrode and the negative electrode, and the non-aqueous electrolyte solution of the present invention.

Specifically, the lithium secondary battery of the present invention may be prepared by injecting the non-aqueous electrolyte solution of the present invention into an electrode assembly which is composed of the positive electrode, the negative electrode, and the separator disposed between the positive electrode and the negative electrode. In this case, those typically used in the preparation of the lithium secondary battery may all be used as the positive electrode, the negative electrode, and the separator which constitute the electrode assembly.

The positive electrode may be prepared by forming a positive electrode material mixture layer on a positive electrode collector. The positive electrode material mixture layer may be prepared by coating the positive electrode collector with a positive electrode slurry including a positive electrode active material, a binder, a conductive agent, and a solvent, and then drying and rolling the coated positive electrode collector.

The positive electrode collector is not particularly limited so long as it has conductivity without causing adverse chemical changes in the battery, and, for example, stainless steel, aluminum, nickel, titanium, fired carbon, or aluminum or stainless steel that is surface-treated with one of carbon, nickel, titanium, silver, or the like may be used.

The positive electrode active material is a compound capable of reversibly intercalating and deintercalating lithium, wherein the positive electrode active material may specifically include a lithium composite metal oxide including lithium and at least one metal such as cobalt, manganese, nickel, or aluminum. Specifically, the lithium composite metal oxide may include lithium-manganese-based oxide (e.g., $LiMnO_2$, $LiMn_2O_4$, etc.), lithium-cobalt-based oxide (e.g., $LiCoO_2$, etc.), lithium-nickel-based oxide (e.g., $LiNiO_2$, etc.), lithium-nickel-manganese-based oxide (e.g., $LiNi_{1-Y}Mn_YO_2$ (where $0<Y<1$), $LiMn_{2-Z}Ni_ZO_4$ (where $0<Z<2$), etc.), lithium-nickel-cobalt-based oxide (e.g., $LiNi_{1-Y1}Co_{Y1}O_2$ (where $0<Y1<1$), lithium-manganese-cobalt-based oxide (e.g., $LiCo_{1-Y2}Mn_{Y2}O_2$ (where $0<Y2<1$), $LiMn_{2-Z1}Co_{Z1}O_4$ (where $0<Z1<2$), etc.), lithium-nickel-manganese-cobalt-based oxide (e.g., $Li(Ni_pCo_qMn_{r1})O_2$ (where $0<p<1$, $0<q<1$, $0<r1<1$, and $p+q+r1=1$) or $Li(Ni_{p1}CO_{q1}Mn_{r2})O_4$ (where $0<p1<2$, $0<q1<2$, $0<r2<2$, and $p1+q1+r2=2$), etc.), or lithium-nickel-cobalt-transition metal (M) oxide (e.g., $Li(Ni_{p2}Co_{q2}Mn_{r3}M_{s2})O_2$ (where M is selected from the group consisting of aluminum (Al), iron (Fe), vanadium (V), chromium (Cr), titanium (Ti), tantalum (Ta), magnesium (Mg), and molybdenum (Mo), and p2, q2, r3, and s2 are atomic fractions of each independent elements, wherein $0<p2<1$, $0<q2<1$, $0<r3<1$, $0<S2<1$, and $p2+q2+r3+S2=1$), etc.), and any one thereof or a compound of two or more thereof may be included.

Among these materials, in terms of the improvement of capacity characteristics and stability of the battery, the lithium composite metal oxide may include $LiCoO_2$, $LiMnO_2$, $LiNiO_2$, lithium nickel manganese cobalt oxide (e.g., $Li(Ni_{1/3}Mn_{1/3}CO_{1/3})O_2$, $Li(Ni_{0.6}Mn_{0.2}Co_{0.2})O_2$, $Li(Ni_{0.5}Mn_{0.3}Co_{0.2})O_2$, $Li(Ni_{0.7}Mn_{0.15}Co_{0.15})O_2$, or $Li(Ni_{0.8}Mn_{0.1}Co_{0.1})O_2$), or lithium nickel cobalt aluminum oxide (e.g., $LiNi_{0.8}Co_{0.15}Al_{0.05}O_2$, etc.).

The positive electrode active material may be included in an amount of 80 wt % to 99.5 wt %, for example, 85 wt % to 95 wt % based on a total weight of solid content in the positive electrode slurry.

In a case in which the amount of the positive electrode active material is 80 wt % or less, since energy density is decreased, capacity may be reduced.

The binder is a component that assists in the binding between the active material and the conductive agent and in the binding with the current collector, wherein the binder is commonly added in an amount of 1 wt % to 30 wt % based on the total weight of the solid content in the positive electrode slurry. Specifically, the binder is added in an amount of 1 part by weight to 50 parts by weight, for example, 3 parts by weight to 15 parts by weight, based on the total weight of the solid content in the positive electrode slurry. If the amount of the binder is less than 1 part by weight, adhesion between the electrode active material and the current collector may be insufficient, and if the amount of the binder is greater than 50 parts by weight, the adhesion may be improved, but, since the amount of the electrode active material is relatively reduced, battery capacity may be lowered.

Examples of the binder may be polyvinylidene fluoride, polyvinyl alcohol, carboxymethylcellulose (CMC), starch, hydroxypropylcellulose, regenerated cellulose, polyvinylpyrrolidone, tetrafluoroethylene, polyethylene, polypropylene, an ethylene-propylene-diene terpolymer (EPDM), a sulfonated EPDM, a styrene-butadiene rubber, a fluoro rubber, various copolymers, and the like.

Furthermore, the conductive agent is a material providing conductivity while not causing chemical changes in the battery, wherein the conductive agent may be added in an amount of 1 wt % to 20 wt % based on the total weight of the solid content in the positive electrode slurry.

As typical examples of the conductive agent, a conductive material, such as: carbon powder such as carbon black, acetylene black, Ketjen black, channel black, furnace black, lamp black, or thermal black; graphite powder such as natural graphite with a well-developed crystal structure, artificial graphite, or graphite; conductive fibers such as carbon fibers or metal fibers; metal powder such as fluorocarbon powder, aluminum powder, and nickel powder; conductive whiskers such as zinc oxide whiskers and potassium titanate whiskers; conductive metal oxide such as titanium oxide; or polyphenylene derivatives, may be used, and those currently sold under the names, such as acetylene black-based conductive agents (Chevron Chemical Company, Denka black (Denka Singapore Private Limited), or Gulf Oil Company), Ketjen black, ethylene carbonate (EC)-based conductive agents (Armak Company), Vulcan XC-72 (Cabot Company), and Super P (Timcal Graphite & Carbon), may be used.

The solvent may include an organic solvent, such as N-methyl-2-pyrrolidone (NMP), and may be used in an amount such that desirable viscosity is obtained when the positive electrode active material as well as selectively the binder and the conductive agent are included. For example, the solvent may be included in an amount such that a concentration of the solid content in the slurry including the positive electrode active material as well as selectively the binder and the conductive agent is in a range of 10 wt % to 60 wt %, for example, 20 wt % to 50 wt %.

Also, the negative electrode may be prepared by forming a negative electrode material mixture layer on a negative electrode collector. The negative electrode material mixture layer may be formed by coating the negative electrode collector with a negative electrode slurry including a negative electrode active material, a binder, a conductive agent, and a solvent, and then drying and rolling the coated negative electrode collector.

The negative electrode collector generally has a thickness of 3 μm to 500 μm. The negative electrode collector is not particularly limited so long as it has high conductivity without causing adverse chemical changes in the battery, and, for example, copper, stainless steel, aluminum, nickel, titanium, fired carbon, copper or stainless steel that is surface-treated with one of carbon, nickel, titanium, silver, or the like, an aluminum-cadmium alloy, or the like may be used. Also, similar to the positive electrode collector, the negative electrode collector may have fine surface roughness to improve bonding strength with the negative electrode active material, and the negative electrode collector may be used in various shapes such as a film, a sheet, a foil, a net, a porous body, a foam body, a non-woven fabric body, and the like.

Furthermore, the negative electrode active material may include at least one selected from the group consisting of lithium metal, a carbon material capable of reversibly intercalating/deintercalating lithium ions, metal or an alloy of lithium and the metal, a metal composite oxide, a material which may be doped and undoped with lithium, and a transition metal oxide.

As the carbon material capable of reversibly intercalating/deintercalating lithium ions, a carbon-based negative electrode active material generally used in a lithium ion secondary battery may be used without particular limitation, and, as a typical example, crystalline carbon, amorphous carbon, or both thereof may be used. Examples of the crystalline carbon may be graphite such as irregular, planar, flaky, spherical, or fibrous natural graphite or artificial graphite, and examples of the amorphous carbon may be soft carbon (low-temperature sintered carbon) or hard carbon, mesophase pitch carbide, and fired cokes.

As the metal or the alloy of lithium and the metal, a metal selected from the group consisting of copper (Cu), nickel (Ni), sodium (Na), potassium (K), rubidium (Rb), cesium (Cs), francium (Fr), beryllium (Be), magnesium (Mg), calcium (Ca), strontium (Sr), silicon (Si), antimony (Sb), lead (Pb), indium (In), zinc (Zn), barium (Ba), radium (Ra), germanium (Ge), aluminum (Al), and tin (Sn), or an alloy of lithium and the metal may be used.

One selected from the group consisting of PbO, $PbO_2$, $Pb_2O_3$, $Pb_3O_4$, $Sb_2O_3$, $Sb_2O_4$, $Sb_2O_5$, GeO, $GeO_2$, $Bi_2O_3$, $Bi_2O_4$, $Bi_2O_5$, $Li_xFe_2O_3$ ($0 \leq x \leq 1$), $Li_xWO_2$ ($0 \leq x \leq 1$), and $Sn_xMe_{1-x}Me'_yO_x$ (Me: manganese (Mn), Fe, Pb, or Ge; Me':Al, boron (B), phosphorus (P), Si, Groups I, II and III elements of the periodic table, or halogen; $0<x \leq 1$; $1 \leq y \leq 3$; $1 \leq z \leq 8$) may be used as the metal composite oxide.

The material, which may be doped and undoped with lithium, may include Si, $SiO_x$ ($0<x<2$), a Si—Y alloy (where Y is an element selected from the group consisting of alkali metal, alkaline earth metal, a Group 13 element, a Group 14 element, transition metal, a rare earth element, and a combination thereof, and is not Si), Sn, $SnO_2$, and Sn—Y (where Y is an element selected from the group consisting of alkali metal, alkaline earth metal, a Group 13 element, a Group 14 element, transition metal, a rare earth element, and a combination thereof, and is not Sn), and a mixture of $SiO_2$ and at least one thereof may also be used. The element Y may be selected from the group consisting of Mg, Ca, Sr, Ba, Ra, scandium (Sc), yttrium (Y), Ti, zirconium (Zr), hafnium (Hf), rutherfordium (Rf), V, niobium (Nb), Ta, dubidium (Db), Cr, Mo, tungsten (W), seaborgium (Sg), technetium (Tc), rhenium (Re), bohrium (Bh), Fe, Pb, ruthenium (Ru), osmium (Os), hassium (Hs), rhodium (Rh), iridium (Ir), palladium (Pd), platinum (Pt), Cu, silver (Ag), gold (Au), Zn, cadmium (Cd), B, Al, gallium (Ga), Sn, In, Ge, P, arsenic (As), Sb, bismuth (Bi), sulfur (S), selenium (Se), tellurium (Te), polonium (Po), and a combination thereof.

The transition metal oxide may include lithium-containing titanium composite oxide (LTO), vanadium oxide, and lithium vanadium oxide.

The negative electrode active material may be included in an amount of 80 wt % to 99 wt % based on a total weight of solid content in the negative electrode slurry.

The binder is a component that assists in the binding between the conductive agent, the active material, and the current collector, wherein the binder is commonly added in an amount of 1 wt % to 30 wt % based on the total weight of the solid content in the negative electrode slurry. Examples of the binder may be polyvinylidene fluoride, polyvinyl alcohol, carboxymethylcellulose (CMC), starch, hydroxypropylcellulose, regenerated cellulose, polyvinylpyrrolidone, tetrafluoroethylene, polyethylene, polypropylene, an ethylene-propylene-diene polymer (EPDM), a sulfonated EPDM, a styrene-butadiene rubber, a fluoro rubber, and various copolymers thereof.

The same material as that used in the preparation of the positive electrode may be used as the conductive agent, wherein the conductive agent may be added in an amount of 1 wt % to 20 wt % based on the total weight of the solid content in the negative electrode slurry.

The solvent may include water or an organic solvent, such as N-methyl-2-pyrrolidone (NMP) and alcohol, and may be used in an amount such that desirable viscosity is obtained when the negative electrode active material as well as selectively the binder and the conductive agent are included. For example, the solvent may be included in an amount such that a concentration of the solid content including the negative electrode active material as well as selectively the binder and the conductive agent is in a range of 50 wt % to 95 wt %, for example, 70 wt % to 90 wt %.

Also, a typical porous polymer film used as a typical separator, for example, a porous polymer film prepared from a polyolefin-based polymer, such as an ethylene homopolymer, a propylene homopolymer, an ethylene-butene copolymer, an ethylene-hexene copolymer, and an ethylene-methacrylate copolymer, may be used alone or in a lamination therewith as the separator. Also, a typical porous nonwoven fabric, for example, a nonwoven fabric formed of high melting point glass fibers or polyethylene terephthalate fibers may be used, but the present invention is not limited thereto.

A shape of the lithium secondary battery of the present invention is not particularly limited, but a cylindrical type using a can, a prismatic type, a pouch type, or a coin type may be used.

Hereinafter, the present invention will be described in more detail according to examples. However, the invention may be embodied in many different forms and should not be construed as being limited to the embodiments set forth herein. Rather, these example embodiments are provided so that this description will be thorough and complete, and will fully convey the scope of the present invention to those skilled in the art.

EXAMPLES

<Preparation of Lithium Secondary Battery>

Example 1

(Non-aqueous Electrolyte Solution Preparation)

A non-aqueous electrolyte solution of the present invention was prepared by adding 5 g of the compound of Formula 1a-1 (n=10, weight-average molecular weight (Mw): 3,000 g/mol) to 95 g of a non-aqueous organic solvent (ethylene carbonate (EC):ethyl methyl carbonate (EMC) =volume ratio of 3:7) in which 1 M $LiPF_6$ was dissolved.

(Secondary Battery Preparation)

94 wt % of $LiNi_{1/3}Co_{1/3}Mn_{1/3}O_2$ (NCM) as a positive electrode active material, 3 wt % of carbon black as a conductive agent, and 3 wt % of polyvinylidene fluoride, as a binder, were added to N-methyl-2-pyrrolidone (NMP), as a solvent, to prepare a positive electrode active material slurry (solid concentration of 50%). An about 20 μm thick aluminum (Al) thin film, as a positive electrode collector, was coated with the positive electrode active material slurry and dried, and the coated Al thin film was then roll-pressed to prepare a positive electrode.

96 wt % of carbon powder as a negative electrode active material, 3 wt % of polyvinylidene fluoride (PVDF) as a binder, and 1 wt % of carbon black, as a conductive agent, were added to NMP, as a solvent, to prepare a negative electrode active material slurry (solid concentration of 80%). A 10 μm thick copper (Cu) thin film, as a negative electrode collector, was coated with the negative electrode active material slurry and dried, and the coated Cu thin film was then roll-pressed to prepare a negative electrode.

An electrode assembly was prepared by sequentially stacking the positive electrode, a separator formed of three layers of polypropylene/polyethylene/polypropylene (PP/PE/PP), and the negative electrode. The electrode assembly was put in a battery case, and the prepared non-aqueous electrolyte solution was injected to prepare a lithium secondary battery (full cell).

Example 2

A non-aqueous electrolyte solution and a secondary battery including the same were prepared in the same manner as in Example 1 except that 10 g of the compound of Formula 1a-1 was added to 90 g of the non-aqueous organic solvent during the preparation of the non-aqueous electrolyte solution.

Example 3

A non-aqueous electrolyte solution and a secondary battery including the same were prepared in the same manner as in Example 1 except that 1 g of the compound of Formula 1a-1 was added to 99 g of the non-aqueous organic solvent during the preparation of the non-aqueous electrolyte solution.

Example 4

A non-aqueous electrolyte solution and a secondary battery including the same were prepared in the same manner as in Example 1 except that 5 g of the compound of Formula 1a-1 (weight-average molecular weight (Mw): 1,000 g/mol) was added to 95 g of the non-aqueous organic solvent during the preparation of the non-aqueous electrolyte solution.

Example 5

A non-aqueous electrolyte solution and a secondary battery including the same were prepared in the same manner as in Example 1 except that 20 g of the compound of Formula 1a-1 was added to 80 g of the non-aqueous organic solvent during the preparation of the non-aqueous electrolyte solution.

Example 6

A non-aqueous electrolyte solution and a secondary battery including the same were prepared in the same manner as in Example 1 except that 5 g of the compound of Formula 1a-1 (weight-average molecular weight (Mw): 10,000 g/mol) was added to 95 g of the non-aqueous organic solvent during the preparation of the non-aqueous electrolyte solution.

Example 7

A non-aqueous electrolyte solution and a secondary battery including the same were prepared in the same manner as in Example 1 except that 0.3 g of the compound of Formula 1a-1 (n=10, weight-average molecular weight (Mw): 3,000 g/mol) was added to 99.7 g of the non-aqueous organic solvent during the preparation of the non-aqueous electrolyte solution.

Example 8

A non-aqueous electrolyte solution and a secondary battery including the same were prepared in the same manner as in Example 1 except that 25 g of the compound of Formula 1a-1 was added to 75 g of the non-aqueous organic solvent during the preparation of the non-aqueous electrolyte solution.

Example 9

A non-aqueous electrolyte solution and a secondary battery including the same were prepared in the same manner as in Example 1 except that 5 g of the compound of Formula 1a-1 (weight-average molecular weight (Mw): 500 g/mol) was added to 95 g of the non-aqueous organic solvent during the preparation of the non-aqueous electrolyte solution.

Example 10

A non-aqueous electrolyte solution and a secondary battery including the same were prepared in the same manner as in Example 1 except that 5 g of the compound of Formula 1a-1 (weight-average molecular weight (Mw): 20,000 g/mol) was added to 95 g of the non-aqueous organic solvent during the preparation of the non-aqueous electrolyte solution.

Comparative Example 1

(Non-aqueous Electrolyte Solution Preparation)

A non-aqueous electrolyte solution was prepared by dissolving 1 M $LiPF_6$ in a non-aqueous organic solvent (ethylene carbonate (EC):ethyl methyl carbonate (EMC)=volume ratio of 3:7).

(Lithium Secondary Battery Preparation)

A lithium secondary battery was prepared in the same manner as in Example 1.

Configurations of the non-aqueous electrolyte solutions of Example 1 to 10 and the non-aqueous electrolyte solution of Comparative Example 1 are summarized in Table 1 below.

TABLE 1

| | Non-aqueous electrolyte solution | | | | |
|---|---|---|---|---|---|
| | Non-aqueous organic solvent | | Oligomer | | |
| | Type | Amount added (g) | Formula | Molecular weight (g/mol) | Amount added (g) |
| Example 1 | EC:EMC = 3:7 volume ratio | 95 | 1a-1 | 3,000 | 5 |
| Example 2 | EC:EMC = 3:7 volume ratio | 90 | 1a-1 | 3,000 | 10 |
| Example 3 | EC:EMC = 3:7 volume ratio | 99 | 1a-1 | 3,000 | 1 |
| Example 4 | EC:EMC = 3:7 volume ratio | 95 | 1a-1 | 1,000 | 5 |
| Example 5 | EC:EMC = 3:7 volume ratio | 80 | 1a-1 | 3,000 | 20 |
| Example 6 | EC:EMC = 3:7 volume ratio | 95 | 1a-1 | 10,000 | 5 |
| Example 7 | EC:EMC = 3:7 volume ratio | 99.7 | 1a-1 | 3,000 | 0.3 |
| Example 8 | EC:EMC = 3:7 volume ratio | 75 | 1a-1 | 3,000 | 25 |
| Example 9 | EC:EMC = 3:7 volume ratio | 95 | 1a-1 | 500 | 5 |
| Example 10 | EC:EMC = 3:7 volume ratio | 95 | 1a-1 | 20,000 | 5 |
| Comparative Example 1 | EC:EMC = 3:7 volume ratio | 100 | — | | — |

EXPERIMENTAL EXAMPLES

Experimental Example 1

High-temperature Performance Evaluation

The lithium secondary batteries of Examples 1 and 2 and Comparative Example 1 were charged at a 0.1 C rate for 3 hours. Subsequently, the lithium secondary batteries were degassed/resealed, charged at 0.2 C to 4.15 V under a constant current/constant voltage condition at room temperature, and discharged at 0.2 C to 3.0 V under a constant current condition to perform initial charge and discharge. After the initial charge and discharge, each battery was charged to 4.15V and stored at 60° C. for 10 weeks (state of charge (SOC) of 100%), and a thickness increase rate (%) at 60° C. was then measured. The results thereof are presented in the FIGURE.

Referring to the thickness increase rates (%) of the FIGURE, with respect to the secondary batteries of Examples 1 and 2 in which the electrolyte solutions including the oligomer according to the embodiment of the present invention were used, it may be confirmed that the thickness increase rates were significantly reduced after 4 weeks at 60° C. in comparison to that of Comparative Example 1 in which the electrolyte solution not including the oligomer was used.

Experimental Example 2

High-temperature Storage Performance

The lithium secondary batteries prepared in Examples 3 to 10 were charged at a 0.1 C rate for 3 hours. Subsequently, the lithium secondary batteries were degassed/resealed, charged at 0.2 C to 4.15 V under a constant current/constant voltage condition at room temperature, and discharged at 0.2 C to 3.0 V under a constant current condition to perform initial charge and discharge. After the initial charge and discharge, each battery was charged to 4.15 V and stored at 60° C. for 6 weeks (SOC of 100%), and capacity retention and thickness increase rate (swelling) of each cell at 6 weeks compared to 0 week were then measured.

The results thereof are presented in Table 2 below.

TABLE 2

|  | Capacity retention (%) | Thickness increase rate (%) |
| --- | --- | --- |
| Example 3 | 94% | 7.2% |
| Example 4 | 95.0% | 6.5% |
| Example 5 | 95.2% | 5.3% |
| Example 6 | 95.8% | 6.8% |
| Example 7 | 82.4% | 15.0% |
| Example 8 | 86.1% | 13.2% |
| Example 9 | 89% | 8.7% |
| Example 10 | 92.5% | 7.0% |

As illustrated in Table 2, it may be understood that the lithium secondary batteries of Examples 3 to 6 had a capacity retention after high-temperature storage of about 94% or more and a thickness increase rate after high-temperature storage of about 7.2% or less.

In contrast, the lithium secondary battery of Example 7, which included the non-aqueous electrolyte solution including a small amount of the additive, had a capacity retention after high-temperature storage of 82.4% or more and a thickness increase rate after high-temperature storage of 15%, wherein it may be understood that the capacity retention and thickness increase rate were deteriorated in comparison to the lithium secondary batteries prepared in Examples 3 to 6.

Also, the lithium secondary battery of Example 8, which included the non-aqueous electrolyte solution including an excessive amount of the additive, had a capacity retention after high-temperature storage of 86.1% or more due to an increase in storage and a thickness increase rate after high-temperature storage of 13.2%, wherein it may be understood that the capacity retention and thickness increase rate were deteriorated in comparison to the lithium secondary batteries prepared in Examples 3 to 6.

Furthermore, the lithium secondary battery of Example 9, which included the non-aqueous electrolyte solution including the oligomer having a low weight-average molecular weight, had a capacity retention after high-temperature storage of 89% or more and a thickness increase rate after high-temperature storage of 8.7%, wherein it may be understood that the capacity retention and thickness increase rate were deteriorated in comparison to the lithium secondary batteries prepared in Examples 3 to 6.

The lithium secondary battery of Example 10, which included the non-aqueous electrolyte solution including the oligomer having a high weight-average molecular weight, had a thickness increase rate of 7% which is equivalent to those of the lithium secondary batteries prepared in Examples 3 to 6, but, since viscosity of the electrolyte solution itself was increased as the molecular weight was increased, wetting properties in the battery were significantly reduced. Thus, charge and discharge efficiency was reduced, and accordingly, it may be understood that the capacity retention was reduced to 92.5% or less due to a non-uniform reaction during high-temperature storage.

The invention claimed is:

1. A non-aqueous electrolyte solution comprising:
a lithium salt;
a non-aqueous organic solvent; and
an oligomer represented by Formula 1 as an additive:

[Formula 1]

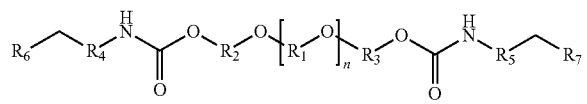

wherein, in Formula 1,
$R_1$ to $R_3$ are each independently a fluorine-substituted or unsubstituted alkylene group having 1 to 4 carbon atoms,
$R_4$ and $R_5$ are each independently an aliphatic hydrocarbon group or an aromatic hydrocarbon group,
$R_6$ and $R_7$ are each independently an alkyl group having 1 to 10 carbon atoms or,

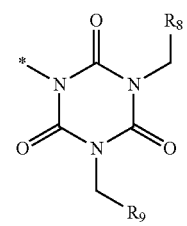

R₈ and R₉ are each independently an alkyl group having 1 to 10 carbon atoms or,

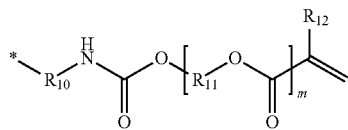

R₁₀ is an aliphatic hydrocarbon group or an aromatic hydrocarbon group,
R₁₁ is an alkylene group having 1 to 3 carbon atoms,
R₁₂ is hydrogen or an alkyl group having 1 to 2 carbon atoms,
n is an integer of 1 to 70, and
m is an integer of 1 to 3.

2. The non-aqueous electrolyte solution of claim 1, wherein, in the oligomer represented by Formula 1,
the aliphatic hydrocarbon groups of R₄, R₅, and R₁₀ comprise an alicyclic hydrocarbon group or a linear hydrocarbon group,
wherein the alicyclic hydrocarbon group is at least one selected from the group consisting of a substituted or unsubstituted cycloalkylene group having 4 to 20 carbon atoms; a substituted or unsubstituted cycloalkylene group having 4 to 20 carbon atoms which contains an isocyanate group (NCO); a substituted or unsubstituted cycloalkenylene group having 4 to 20 carbon atoms; and a substituted or unsubstituted heterocycloalkylene group having 2 to 20 carbon atoms, and
wherein the linear hydrocarbon group is at least one selected from the group consisting of a substituted or unsubstituted alkylene group having 1 to 20 carbon atoms; a substituted or unsubstituted alkylene group having 1 to 20 carbon atoms which contains an isocyanate group (NCO); a substituted or unsubstituted alkoxylene group having 1 to 20 carbon atoms; a substituted or unsubstituted alkenylene group having 2 to 20 carbon atoms; and a substituted or unsubstituted alkynylene group having 2 to 20 carbon atoms, and
the aromatic hydrocarbon groups of R₄, R₅, and R₁₀ comprise a substituted or unsubstituted arylene group having 6 to 20 carbon atoms; or a substituted or unsubstituted heteroarylene group having 2 to 20 carbon atoms.

3. The non-aqueous electrolyte solution of claim 1, wherein the oligomer represented by Formula 1 comprises an oligomer represented by Formula 1a:
[Formula 1a]
wherein, in Formula 1a,
R₄ and R₅ are each independently an aliphatic hydrocarbon group,
R₈ and R₉ are each independently,
R₁₀ is an aliphatic hydrocarbon group,
R₁₁ is an alkylene group having 1 to 3 carbon atoms,
R₁₂ is hydrogen or an alkyl group having 1 to 2 carbon atoms,
n is an integer of 10 to 20, and
m is an integer of 1 to 2.

4. The non-aqueous electrolyte solution of claim 3, wherein the oligomer represented by Formula 1a comprises an oligomer represented by Formula 1a-1:
[Formula 1a-1]
wherein, in Formula 1a-1,
n is an integer of 10 to 20.

5. The non-aqueous electrolyte solution of claim 1, wherein the oligomer represented by Formula 1 is included in an amount of 0.5 wt % to 20 wt % based on a total weight of the non-aqueous electrolyte solution.

6. The non-aqueous electrolyte solution of claim 5, wherein the oligomer represented by Formula 1 is included in an amount of 1 wt % to 10 wt % based on the total weight of the non-aqueous electrolyte solution.

7. The non-aqueous electrolyte solution of claim 1, wherein the oligomer represented by Formula 1 has a weight-average molecular weight (Mw) of 1,000 g/mol to 10,000 g/mol.

8. The non-aqueous electrolyte solution of claim 7, wherein the oligomer represented by Formula 1 has a weight-average molecular weight (Mw) of 3,000 g/mol to 8,000 g/mol.

9. The non-aqueous electrolyte solution of claim 8, wherein the oligomer represented by Formula 1 has a weight-average molecular weight (Mw) of 3,000 g/mol to 5,000 g/mol.

10. A lithium secondary battery comprising a negative electrode, a positive electrode, a separator disposed between the negative electrode and the positive electrode, and the non-aqueous electrolyte solution of claim 1.

11. The non-aqueous electrolyte solution of claim 1, wherein the non-aqueous organic solvent is selected from the group consisting of an ether-based solvent, an ester-based solvent, an amide-based solvent, and mixtures of two or more thereof.

12. The non-aqueous electrolyte solution of claim 11, wherein the ester-based solvent is selected from the group consisting of a cyclic carbonate compound, a linear carbonate compound, a linear ester compound, a cyclic ester compound, and mixtures of two or more thereof.

13. The non-aqueous electrolyte solution of claim 12, wherein the cyclic carbonate compound is selected from the group consisting of ethylene carbonate (EC), propylene carbonate (PC), 1,2-butylene carbone, 2,3-butylene carbonate, 1,2-pentylene carbonate, 2,3-pentylene carbonate, vinylene carbonate, fluoroethylene carbonate (FEC), and mixtures of two or more thereof.

14. The non-aqueous electrolyte solution of claim 12, wherein the linear carbonate compound is selected from the group consisting of dimethyl carbonate (DMC), diethyl carbonate (DEC), dipropyl carbonate, ethylmethyl carbonate (EMC), methylpropyl carbonate, ethylpropyl carbonate, and mixtures of two or more thereof.

* * * * *